United States Patent [19]

Valerio

[11] Patent Number: 4,834,743
[45] Date of Patent: May 30, 1989

[54] AUTOLOGOUS TRANSFUSION SYSTEM AND APPARATUS

[75] Inventor: Michael A. Valerio, Wallingford, Conn.

[73] Assignee: Sherwood Medical Company, St. Louis, Mo.

[21] Appl. No.: 928,448

[22] Filed: Nov. 10, 1986

[51] Int. Cl.$^4$ .............................................. A61B 19/00
[52] U.S. Cl. ..................................... 604/403; 604/406
[58] Field of Search ...................... 604/4, 5, 403, 406, 604/408, 411, 412, 413, 414, 262, 252, 319; 128/760

[56] References Cited

U.S. PATENT DOCUMENTS

| | | | |
|---|---|---|---|
| 2,682,268 | 6/1954 | Ryan et al. ................................. | 604/5 |
| 4,033,345 | 7/1977 | Sorenson et al. ......................... | 604/4 |
| 4,035,304 | 7/1977 | Watanabe ............................. | 604/406 |
| 4,047,526 | 9/1977 | Reynolds et al. ........................ | 604/4 |
| 4,445,884 | 5/1984 | Kurtz et al. .............................. | 604/4 |
| 4,596,571 | 6/1986 | Bellotti et al. ....................... | 604/411 |
| 4,747,844 | 5/1988 | Elliot .................................... | 604/319 |

OTHER PUBLICATIONS

Pleur—Evac Auto Transfusion System, Deknatel Division Pfizer Hospital Products, Floral Park, NY 11001.
Catalog Cut, "Why Transfuse if You Can Reinfuse with Pleur-Evac TM Auto Transfusion System?", DeKratel Div. of Pfizer Hospital Products Group, Floral Park, NY 11001.
"An Improved Method for Collection of Shed Mediastinal Blood for Autotransfusion", Voegole, M. D., et al., Society for Thoracic Surgeons, 1981.

*Primary Examiner*—C. Fred Rosenbaum
*Assistant Examiner*—J. L. Kruter
*Attorney, Agent, or Firm*—Stanley Garber; Andrew Beck; Richard Allison

[57] ABSTRACT

A transfer bag apparatus is disclosed which is adapted to be used in the autologous transfusion of blood to a patient by collecting the blood from a primary blood reservoir (e.g., the collection chamber of a drainage device for the chest cavity of the patient or a cardiotomy reservoir). The transfer bag comprises a flexible bag, having means on one part of the bag to be placed in fluid-tight communication with an infusion set to transfuse the patient with blood, and spike means on another part of the bag adapted to be placed in fluid-tight communication with the interior of the primary blood reservoir to transfer blood to the interior of the blood bag. The method of autologously transfusing a patient by means of the present invention involves collecting blood from the patient in the primary blood reservoir, placing the transfer bag assembly in communication with the blood contained in the reservoir by means of the spike inlet means, transferring the collected blood from the reservoir to the transfer bag, and allowing the blood collected in the transfer bag to be infused into the patient.

2 Claims, 1 Drawing Sheet

AUTOLOGOUS TRANSFUSION SYSTEM AND APPARATUS

BACKGROUND OF THE PRESENT INVENTION

1. Field of the Invention

The present invention relates to the autologous transfusion of blood to a patient from a primary blood drainage reservoir, e.g., the collection chamber of a drainage device for the chest cavity of the patient, a cardiotomy reservoir, or the like, by means of a transfer bag apparatus having a spike inlet adapted to be placed in fluid-tight communication with the primary blood drainage reservoir.

2. Description of the Prior Art

The transfer bag of the present invention is generally useful in autologous transfusion where blood is first removed from a patient into a primary blood drainage reservoir. Two examples of such reservoirs will be described hereinafter. The present invention relates to the use of a blood transfer bag, of a particular design, which is adapted to be placed in fluid-tight communication with the interior of a primary blood drainage reservoir to allow for transfer of blood from the reservoir into the transfer blood bag. The transfer blood bag also has separate means which are adapted to be connected with an infusion set to infuse the patient with the collected blood.

One example of a primary blood reservoir is a cardiotomy reservoir of the type shown in The Annals of Thoracic Surgery, Vol. 40, No. 5, November 1985, pp. 519-520. The spike means on the transfer blood bag described herein can be placed into the outlet port or tubing of such a reservoir, if desired, to receive the blood for eventual reinfusion into the patient.

Another type of primary blood drainage reservoir adapted to be used herein is the collection chamber of an underwater drainage device for the chest cavity of a patient. It is known to collect fluid, blood and gases from the chest cavity between the lung and the surrounding rib cage of a patient. Various type of apparatus are used for such a purpose. Generally, "one-bottle", "two-bottle", and "three-bottle" collection systems are known. U.S. Pat. No. 4,605,400 to L. D. Kurtz et al. illustrates a recent device of this type. Often, such devices have sampling ports (e.g., equipped with latex diaphragms) in the wall of the collection chamber which can be accessed with the blood transfer bag of the present invention.

Autologous blood transfusion processes, using transfer blood bags, which differ in design from the present bag, are described in the literature.

U.S. Pat. No. 4,006,745 describes an autologous transfusion system and method which contemplates the use of a flexible transfer bag which functions to receive blood from a second receptacle in a dual receptable blood-receiving apparatus. There is no suggestion of using the transfer bag with the collection chamber of a chest drainage device or with a cardiotomy reservoir. Also, the transfer bag shown in this patent differs from the bag of the present invention since it has a single opening or puncture site to both receive blood from the receptacle as well as later serve as a point of attachment for a transfusion set. This puncture side is also not in the form of a spike adapted to be placed in fluid-tight communication with either a chest drainage collection chamber or with a cardiotomy reservoir.

U.S. Pat. No. 3,866,608 illustrates, in FIG. 5, for example, a suction collection system which utilizes a lower blood reservoir bag made of flexible material which contains two openings to receive blood from an upper reservoir and to connect to an infusion set, respectively. The inwardly projecting sleeve in this bag which is adapted to receive an extending tube from an upper collection (or primary) reservoir is, again, not designed or adapted to be placed in fluid-tight communication with a chest drainage collection chamber (such as those having sampling ports which need to be pierced) or with a cardiotomy reservoir.

SUMMARY OF THE PRESENT INVENTION

THe present invention relates to a transfer bag apparatus which is adapted to be used in the autologous transfusion of blood to a patient by collecting blood from a primary blood reservoir (e.g., the collection chamber in the aforementioned types of drainage devices for the chest cavity of a patient or a cardiotomy reservoir). The transfer bag of the present invention comprises a flexible blood bag having means at one position thereon which are adapted to be placed in fluid-tight communication with an infusion set to thereby reinfuse the patient with blood collected in the transfer bag from the primary blood reservoir and with spike means at a separate position on the bag which are especially adapted to be placed in fluid-tight communication with the interior of the primary blood reservoir (e.g., the chest drainage collection chamber or cardiotomy reservoir) to transfer blood collected in the primary blood reservoir to the interior of the transfer blood bag.

The present invention also encompasses the combination of the primary blood reservoir and the transfer bag apparatus.

The present invention, moreover, relates to a method of autologously transfusing a patient which comprises the collection of blood from the patient into the primary blood reservoir, placing the transfer bag apparatus of the present invention in fluid-tight communication with the blood collected in the primary blood reservoir, transferring the collected blood from the reservoir to the transfer bag, and allowing the blood collected in the transfer bag to be reinfused into the patient by means of a conventional infusion set.

DESCRIPTION OF THE DRAWINGS

The present application will be further understood by reference to the Drawings which form a portion of the present specification wherein.

DETAILED DESCRIPTION OF THE PRESENT INVENTION

Figure 2:
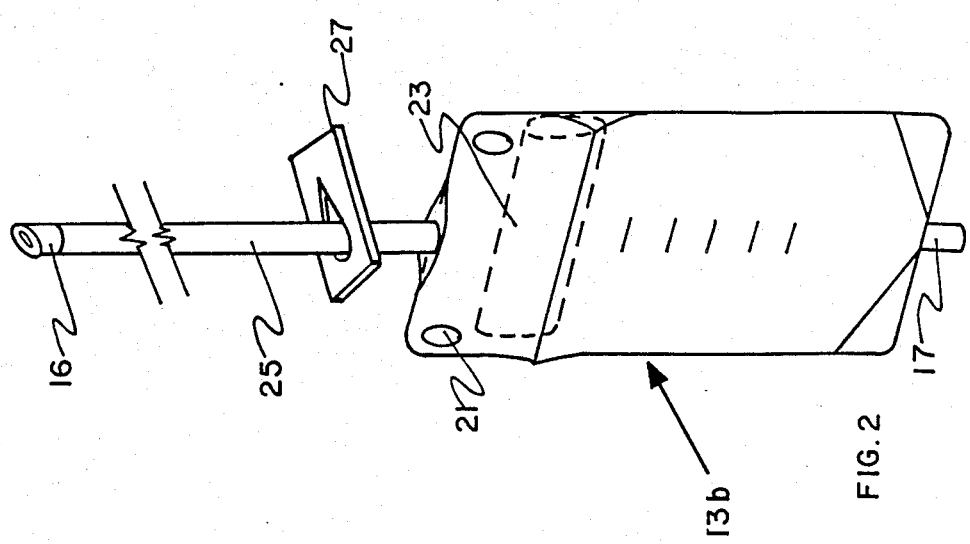
FIGS. 1 and 2 are each perspective views of an embodiment of a transfer bag apparatus of the present invention which is adapted to be used with a primary blood reservoir in practicing the method described herein.
Figure 1:
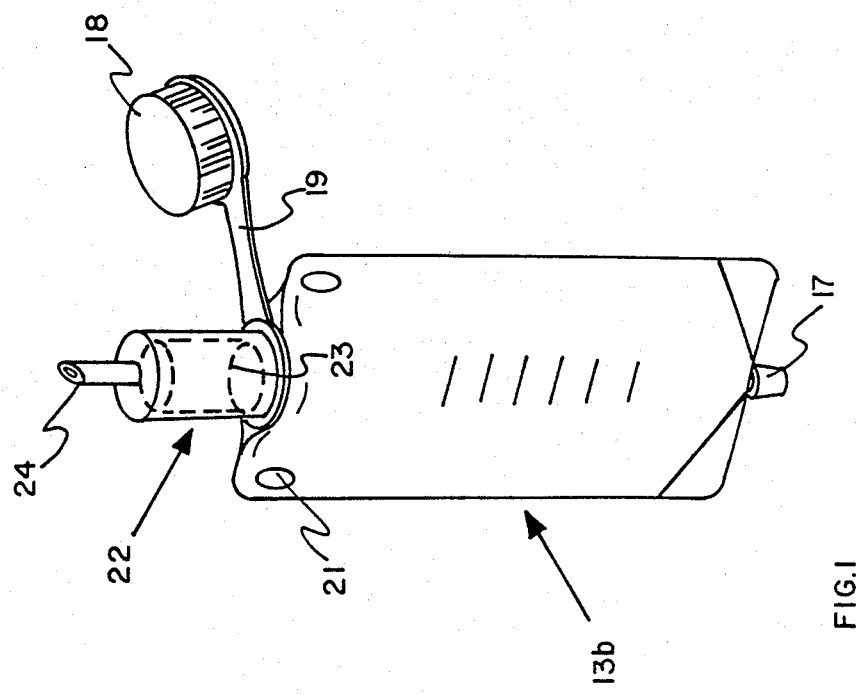

In order to utilize the transfer bag apparatus shown in FIGS. 1 and 2, the person of ordinary skill in the art would first collect blood from a patient in a primary blood reservoir (e.g., in a collection chamber for one of the types of chest drainage device described before or into a cardiotomy reservoir). Once this has been accomplished, the reservoir is placed in fluid-tight communication with the transfer blood bag shown in either FIGS. 1 or 2 by using the spike inlet means on the transfer bag (e.g., to spike a sampling port, pierce an outlet port, etc.). Once the blood is transferred from the reservoir to the transfer bag 13(b), the preferred sterile cover is removed from the closure plug covering the site for the infusion set and blood is reinfused into the patient in a known manner. The transfusion can take place by appropriately suspending the blood bag via appropriate hole means 21 on an appropriate transfusion stand and thereafter connecting a suitable infusion set to the spike port contained at the other end of the bag after removal of the preferred cover. The Drawings show the spike port with the cover attached to it and designates this combination with reference numeral 17.

The Drawings show two alternative embodiments which can be used with the desired primary blood reservoir. The bag 13(b) is made of appropriate flexible material (e.g., plastic). It is provided with a removable housing 22 (which can be rigid, if desired) which can contain a blood filter 23 therein and which terminates at its uppermost end in a spike 24 which is adapted to be placed, for example, through the sampling port in a collection chamber for an underwater chest drainage device, to allow for egress of blood therefrom through the filter means 23 into the infusion bag 13(b). Closure 18 is preferably connected via member 19 to allow for closure of the opening into which housing 23 fits if it is desired to store the bag and blood prior to infusion of the blood into the patient.

The embodiment shown in FIG. 2 differs in that the blood filter 23 is placed within the infusion blood bag body. The means which are adapted to convey blood from the primary blood reservoir comprise tubing 25 which terminates in a spike 16 which is adapted to be placed, for example, through the sampling port of a collection chamber to allow blood to flow into the infusion blood bag 13(b). A slide clamp 27 is provided to pinch off the flexible tubing to prevent further flow of blood through the tube, if desired. In both embodiments shown, the spike means (24 in FIG. 1 and 25, 16 in FIG. 2) can be made to be more rigid than flexible so as to have the strength to pierce, for example, any sampling port desired.

The foregoing has been presented to illustrate certain embodiments of the present invention, but should not be construed in a limiting sense. The scope of protection that is sought is set forth in the claims which follow.

I claim:
1. A transfer blood bag comprising:
 (a) a bag having flexible sides and a fluid-tight interior adapted to contain blood;
 (b) an outlet means on said bag for connection to an infusion set for fluid-tight communication of the interior of said bag with said infusion set;
 (c) an opening means on said bag for detachable connection to one portion of a housing for fluid-tight communication of the interior of said bag with a fluid-tight interior of said housing;
 (d) an inlet means on a separate portion of said housing for fluid-tight communication with a source of blood;
 (e) a closure means on said bag for sealing the opening means when said housing is detached therefrom; and
 (f) said closure being a cap tethered to said bag proximate said opening.
2. A transfer blood bag comprising:
 (a) a bag having flexible sides and a fluid-tight interior adapted to contain blood;
 (b) an outlet means on said bag for connection to an infusion set for fluid-tight communication of the interior of said bag with said infusion set;
 (c) an opening means on said bag for detachable connection to one portion of a housing for fluid-tight communication of the interior of said bag with a fluid-tight interior of said housing;
 (d) an inlet means on a separate portion of said housing for fluid-tight communication with a source of blood;
 (e) a closure means on said bag for sealing the opening means when said housing is detached therefrom; and
 (f) filter means, operatively disposed within said housing and detachable from said bag, for filtering blood transferred from said source of blood through said housing into the interior of said bag;
 (g) said inlet being in the form of a spike, said spike being more rigid than said bag sides; and
 (h) said closure being a cap tethered to said bag proximate said opening.

* * * * *